US006534262B1

(12) United States Patent
McKernan et al.

(10) Patent No.: US 6,534,262 B1
(45) Date of Patent: Mar. 18, 2003

(54) SOLID PHASE TECHNIQUE FOR SELECTIVELY ISOLATING NUCLEIC ACIDS

(75) Inventors: Kevin McKernan, Cambridge, MA (US); Paul McEwan, Cambridge, MA (US); William Morris, Cleveland Hts., OH (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/311,317

(22) Filed: May 13, 1999

Related U.S. Application Data

(60) Provisional application No. 60/121,779, filed on Feb. 26, 1999, and provisional application No. 60/085,480, filed on May 14, 1998.

(51) Int. Cl.[7] .......................... C12Q 1/68; G01N 33/53; G01N 33/537; G01N 33/543; C07H 21/00
(52) U.S. Cl. .......................... 435/6; 435/7.5; 435/7.94; 536/25.4
(58) Field of Search .......................... 435/6, 7.5, 7.94; 536/25.4

(56) References Cited

U.S. PATENT DOCUMENTS

| | | | |
|---|---|---|---|
| 5,234,809 A | | 8/1993 | Boom et al. .................. 435/91 |
| 5,561,064 A | | 10/1996 | Marquet et al. .......... 435/320.1 |
| 5,614,386 A | * | 3/1997 | Metzker et al. ............. 435/91.1 |
| 5,665,554 A | | 9/1997 | Reeve et al. .................... 435/6 |
| 5,705,628 A | * | 1/1998 | Hawkins ..................... 536/25.4 |
| 5,808,041 A | | 9/1998 | Padhye et al. .............. 536/25.4 |
| 5,898,071 A | | 4/1999 | Hawkins ..................... 536/25.4 |

FOREIGN PATENT DOCUMENTS

| | | |
|---|---|---|
| WO | WO 91/12079 | 8/1991 |
| WO | WO 95/21250 | 8/1995 |
| WO | WO 96/09379 | 3/1996 |
| WO | WO 96/18731 | 6/1996 |
| WO | WO 98/05767 | 2/1998 |
| WO | WO 98/16653 | 4/1998 |
| WO | WO 98/31840 | 7/1998 |

OTHER PUBLICATIONS

Cole, "Purification of plasmid and high molecular mass DNA using PEG–salt two–phase extraction," *Bio Techniques*, (1991), vol. 11, No. 1, pp. 18, 20, 22, 24.*

Heller et al., "Capillary electrophoresis of proteins and nucleic acids in gels and entangled polymer solutions", *Journal of Chromatography*, (1995), vol. 698, pp. 19–31.*

Dynal Catalog, pp. 78–79 and 138, 1995.*

Sambrook et al., "Molecular Cloning",Cold Spring Harbor Laboratory Press, pp. 11.33 and E.10, 1989.*

Hawkins, T.L., et al., "DNA purification and isolation using a solid–phase," *Nucleic Acids Research*, 22(21):4543–4544 (1994).

Levison, P.R., et al., "Recent developments of magnetic beads for use in nucleic acid purification," *Journal of Chromatography A*, 816:107–111 (1998).

Birnboim, H.C., and Doly, J., "A rapid alkaline extraction procedure for screening recombinant plasmid DNA," Nucleic Acids Research, 7(6):1513–1523 (1979).

Birnboim, H.C., "A Rapid Alkaline Extraction Method for the Isolation of Plasmid DNA," *Methods in Enzymology*, 100:243–255 (1983).

Boom, R., et al., "Rapid and Simple Method for Purification of Nucleic Acids," *Journal of Clinical Microbiology*, 28(3):495–503 (1990).

Fry, G., et al., "A New Approach to Template Purification for Sequencing Applications Using Paramagnetic Particles," *BioTechniques*, 13(1):124–131 (1992).

Deggerdal, A., and Larsen, F., "Rapid Isolation of PCR–Ready DNA from Blood, Bone Marrow and Cultured Cells, Based on Paramagnetic Beads," *BioTechniques*, 22:554–557 (Mar. 1997).

Pulleyblank, D., et al., "A method for the purification of E. coli plasmid DNA by homogeneous lysis and polyethylene glycol precipitation," *Molec. Biol. Rep.*, 9:191–195 (1983).

Hawkins, T.L., et al., "A Magnetic Attraction to High–Throughput Genomics," *Science*, 276:1887–1890 (Jun. 20, 1997).

(List continued on next page.)

Primary Examiner—W. Gary Jones
Assistant Examiner—Arun K. Chakrabarti
(74) Attorney, Agent, or Firm—Hamilton, Brook, Smith & Reynolds, P.C.

(57) ABSTRACT

A method of isolating target nucleic acid molecules from a solution comprising a mixture of different size nucleic acid molecules, in the presence or absence of other biomolecules, by selectively facilitating the adsorption of a particular species of nucleic acid molecule to the functional group-coated surface of magnetically responsive paramagnetic microparticles is disclosed. Separation is accomplished by manipulating the ionic strength and polyalkylene glycol concentration of the solution to selectively precipitate, and reversibly adsorb, the target species of nucleic acid molecule, characterized by a particular molecular size, to paramagnetic microparticles, the surfaces of which act as a bioaffinity adsorbent for the nucleic acids. The target nucleic acid is isolated from the starting mixture based on molecular size and through the removal of magnetic beads to which the target nucleic acid molecules have been adsorbed. The disclosed method provides a simple, robust and readily automatable means of nucleic acid isolation and purification which produces high quality nucleic acid molecules suitable for: capillary electrophoresis, nucleotide sequencing, reverse transcription cloning the transfection, transduction or microinjection of mammalian cells, gene therapy protocols, the in vitro synthesis of RNA probes, cDNA library construction and PCR amplification.

34 Claims, No Drawings

OTHER PUBLICATIONS

Hawkins, T., "M13 single-strand purification using a biotinylated probe and streptavidin coated magnetic beads," *J. DNA Sequencing and Mapping*, 3:65–69 (1992).

Lis, J.T., "Fractionation of DNA Fragments by Polyethylene Glycol Induced Precipitation," *Methods in Enzymology*, 65:347–353 (1980).

Paithankar, K.R., and Prasad, K.S.N., "Precipitation of DNA by polyethylene glycol and ethanol," *Nucleic Acids Research*, 19(6):1346 (1991).

Alderton, R.P., et al., "Magnetic Bead Purification of M13 DNA Sequencing Templates," *Analytical Biochemistry*, 201:166–169 (1992).

* cited by examiner

SOLID PHASE TECHNIQUE FOR SELECTIVELY ISOLATING NUCLEIC ACIDS

RELATED APPLICATION(S)

This application claims the benefit of Provisional Application No.: 60/085,480, entitled "Solid Phase Technique for Isolating and Purifying Plasmids" by Kevin McKernan and Paul McEwan, filed May 14, 1998 and Provisional Application No. 60/121,779 entitled "Solid Phase Technique for Selectively Isolating Nucleic Acids" by Kevin McKeman and Paul McEwan, filed on Feb. 26, 1999. The entire teachings of the referenced applications are incorporated herein by reference.

GOVERNMENT SUPPORT

The invention was supported, in whole or in part, by a National Human Genome Research Institute Grant, Grant Number 5P 50 HG00098-09, from the National Institutes of Health. The United States Government has certain rights in the invention.

BACKGROUND OF THE INVENTION

Many molecular biology applications, such as capillary electrophoresis, nucleotide sequencing, reverse transcription cloning and gene therapy protocols, which contemplate the transfection, transduction or microinjection of mammalian cells, require the isolation of high quality nucleic acid preparations. Quality is a particularly important factor for capillary electrophoresis for all sequencing methods and for gene therapy protocols. Quantity is an equally important consideration for some applications, for example, large scale genomic mapping and sequencing projects, which require the generation of hundreds of thousands of high quality DNA templates.

Extension product quality is crucial to the success of automated dye-labeled dideoxynucleotide sequencing methods, such as those described in Maniatis, T., et al., *Molecular Cloning: A Laboratory Manual*, 2nd Edition, Cold Spring Harbor Laboratories, Cold Spring Harbor, N.Y., Sanger, E., et al., *Proc. Natl. Acad Sci.* 74:5463–5467 (1977), and Mierendorf, R. and Pfeffer, D. Methods Enzymol. 152:5556–562 (1987), and is a particularly critical consideration for capillary electrophoresis protocols. The isolation of high quality nucleic acid preparations from starting mixtures of diverse composition and complexity is a fundamental technique in molecular biology.

The advent of demanding molecular biology applications has increased the need for high-throughput, and preferably readily automatable, purification protocols capable of producing high quality nucleic acid preparations. Although recent technological advancements and the advent of robotics have facilitated the automation of sequencing reactions and gel reading steps, throughput is still limited by the availability of readily automatable methods of nucleic acid purification.

SUMMARY OF THE INVENTION

The present invention is a method of separating different species of nucleic acid molecules present in a mixture, which can be a solution or a suspension, on the basis of differences in their molecular size. Separation is accomplished by selectively adsorbing target nucleic acid molecules (e.g., targeted or selected for isolation or purification), present in a mixture to a magnetically responsive solid phase carrier such as paramagnetic microparticles. In addition to target nucleic acid molecules the mixture can comprise other components, which include, but are not limited to, other non-target nucleic acid molecules, proteins, cell components, and reagents or chemicals used in methods in which the nucleic acids are processed or used. That is, the mixture can comprise a wide variety of types of molecules, from which target nucleic acid molecules are separated, by the present method on the basis of differences in molecular size. Thus, the invention discloses a method useful for isolating a particular species of nucleic acid molecule from a mixture. The nucleic acid to be isolated (e.g., separated or purified) (referred to as target nucleic acids or target nucleic acid molecules) are separated from the rest of the mixture based on molecular size and through the physical removal of the solid phase carrier to which the target nucleic acid molecules have been adsorbed according to the method described herein.

The present invention provides a method of selectively isolating (e.g., purifying) a species of nucleic acid molecule, based on its molecular size, from a mixture. This embodiment of the invention involves selectively precipitating and facilitating the adsorption of a target species of nucleic acid molecule to the functional group coated surface of a solid phase carrier. Purification of the target nucleic acids is accomplished by applying an external force which results in the removal (e.g., separation) of the solid phase carrier from the mixture in which the carriers have been suspended. In a preferred embodiment, the solid phase carrier is a paramagnetic microparticle and separation is accomplished by magnetic means.

The present invention is useful to isolate, from a mixture from which at least one species of nucleic acid molecule has been selectively removed, one or more additional (e.g., a second, third, fourth etc.) species of nucleic acid molecules which are of a smaller molecular size than the one or more target nucleic acid species which have already been removed from an initial (or starting) mixture by the method described herein. The additional species of nucleic acid molecule targeted for isolation in this additional embodiment remained soluble in the presence of the PEG and salt concentrations used to isolate the larger nucleic acid molecule and, therefore, will still be present in the mixture from which the first target nucleic acid molecule has been removed.

In an alternative embodiment of the instant invention, two or more species of nucleic acid molecule present in the same mixture, which differ in molecular size from each other by at least a factor of two, are separated from each other. The method described herein is used to isolate a particular species (e.g., a target species) of nucleic acid molecules of virtually any size, present in a wide variety of sources, from other nucleic acid molecules which are also present in the mixture. For example, the method disclosed herein can be used to isolate recombinant nucleic acid species, produced in host cells, including selective RNA precipitations based on molecular size, or replicative form DNA produced by a virus during lytic replication from endogenous host cell nucleic acid species. The method can also be used to isolate a particular species of nucleic acid from a solution resulting from a restriction enzyme digestion or an agarose solution containing nucleic acid. Alternatively, the method disclosed herein provides a size selection purification scheme suitable for use after a DNA shearing process (e.g., hydroshearing or sonication), thereby providing an alternative to the more traditional method of gel electrophoresis and band excision which are conventionally used to isolate a species of nucleic acid molecule targeted for purification. The disclosed method also finds utility as a method of separating multiplex PCR products, or as a sequencing reaction detemplating protocol. For example, using the method disclosed herein solid phase magnetically responsive paramagnetic microparticles can be used to selectively remove sequencing products and DNA templates from sequencing samples.

The present invention is also useful to isolate, from a mixture from which at least one species of nucleic acid molecule has been selectively removed, one or more additional (e.g., a second, third, fourth etc.) species of nucleic acid molecules which are of a smaller molecular size than the one or more target nucleic acid species which have already been removed from an initial (or starting) mixture by the method described herein. The additional species of nucleic acid molecule targeted for isolation in this additional embodiment remained soluble in the presence of the PEG and salt concentrations used to isolate the larger nucleic acid molecule and, therefore, will still be present in the mixture from which the first target nucleic acid molecule has been removed.

One embodiment of the instant invention provides a method of selectively isolating a target species of nucleic acid molecule from a host cell lysate which is a mixture of target nucleic acid molecules, non-target nucleic acid molecules and other cellular components. The presence of these other components (e.g., cellular components, reagents or biomolecules) could have an adverse effect on the downstream molecular biology application for which the target nucleic acids are being prepared. For example, the present method is useful to selectively isolate exogenous nucleic acid from endogenous host cell nucleic acid molecules. More specifically, the present method is useful to selectively isolate recombinant DNA, produced by the replication of exogenous DNA in an appropriate host cell, from endogenous host cell DNA and from other host cell components. Exogenous DNA (e.g., recombinant or plasmid DNA) can be introduced into suitable host cells, or their ancestors, by a vector, such as a bacterial artificial chromosome (BAC), a yeast artificial chromosome (YAC), a phage artificial chromosome (PAC), a P1, a cosmid (plasmids with λ phage packaging sites) or a bacterial plasmid. The exogenous DNA replicates in the host cell and can be isolated from host cell DNA using the method described herein. Initially, host cell (endogenous) DNA is removed through the use of appropriate concentrations of PEG and salt. Subsequently, exogenous nucleic acid molecules targeted for isolation are removed, again through the use of appropriate concentrations of PEG and salt. In this embodiment, as well as in all others described herein, nucleic acid molecules of varying sizes can be removed from a mixture sequentially. That is, all nucleic acid molecules above a certain size cutoff can be removed through the use of appropriate PEG and salt concentrations, with the result that smaller nucleic acid molecules remain in the mixture. This process can be repeated to remove progressively smaller nucleic acid molecules. According to this embodiment, exogenous nucleic acid molecules are selectively isolated from endogenous host cell nucleic acid molecules and other biomolecules present in a host cell lysate. More specifically, this embodiment comprises combining functional group-coated paramagnetic microparticles and suitable concentrations of a precipitating reagent, for example, a polyalkylene glycol, and a salt to result in the facilitated adsorption of endogenous nucleic acid (e.g., host cell genomic DNA) present in the mixture, to the surfaces of the microparticles suspended therein, and the subsequent removal, such as by magnetic means, of the microparticles from the resulting combination.

The removal of the microparticle having host cell genomic DNA (e.g., endogenous DNA) adsorbed to its surfaces from the combination results in the concomitant separation of the target nucleic acid selected for isolation from other relatively smaller-sized nucleic acids (e.g., exogenous nucleic acids), which remain in solution, thereby producing a mixture that is enriched for exogenous nucleic acid. The resulting PEG-facilitated adsorption of the precipitated host cell DNA to the functional group-coated surfaces of the paramagnetic microparticles (which can be considered a preclearance of host cell DNA) is rapid; it is generally complete within thirty seconds. Exogenous target nucleic acid molecules present in the mixture enriched for relatively smaller-sized nucleic acids can subsequently be isolated from the mixture by performing a second PEG-induced precipitation, according to the method provided herein.

The present invention further relates to a method of isolating an exogenous DNA template (e.g., a plasmid DNA template) suitable for use in either manual or a high-throughput automated sequencing methods. In general terms this method comprises: treating host cells which contain exogenous DNA (e.g., plasmid DNA) with an alkali and detergent (e.g., sodium dodecyl sulphate (SDS)) combination, thus producing a lysed host cell suspension; suspending paramagnetic microparticles which bind DNA (e.g., have an affinity for DNA) in the lysed host cell suspension in the presence of sufficient concentrations of a DNA precipitating reagent, for example, polyethylene glycol, and a salt to selectively precipitate and adsorb host cell DNA (e.g., genomic DNA), but not exogenous DNA, to the surfaces of the paramagnetic microparticles; removing the microparticles having host cell DNA bound thereto from the suspension, preferably by magnetic means, thereby producing a plasmid DNA-enriched supernatant; combining additional paramagnetic microparticles having an affinity for DNA with the resulting plasmid DNA-enriched supernatant; and adjusting the precipitating reagent and/or salt concentration of this supernatant to suitable levels to result in the selective precipitation and adsorption of exogenous (e.g., plasmid) DNA to the microparticles suspended therein. As a result, exogenous (e.g., plasmid) DNA is bound to the microparticles, thereby producing microparticle-bound exogenous DNA.

The purity of the microparticle-bound exogenous DNA can be improved by washing the particle-bound nucleic acid molecules to remove other host cell biomolecules by contacting the microparticles with a high ionic strength wash buffer which dissolves, for example impurities (e.g., proteins, reagents or chemicals) adsorbed to the paramagnetic microparticles, but does not solubilize the adsorbed DNA. As a result, the exogenous DNA targeted for isolation remains adsorbed to the solid phase carrier surface. The washed, particle-bound exogenous DNA template can subsequently be removed from the solid phase carrier by contacting the washed microparticles with an elution buffer which solubilizes the adsorbed DNA, thereby preparing plasmid DNA suitable for use as a DNA nucleotide sequencing template.

In one embodiment, the invention is a readily automatable method of isolating a plasmid DNA template for nucleotide sequencing. The use of paramagnetic microparticles having functional group-coated surfaces as a bioaffinity adsorbent for nucleic acid molecules affords an alternative, and readily automatable, means of molecular separation useful in the design of a solid phase technique for the selective isolation of nucleic acid molecules targeted for isolation. A particular advantage of the disclosed method is that it obviates the necessity of centrifugation and filtration steps and the use of organic solvents. In addition, the ample surface area provided by suitable solid phase carriers allows the volume of the reactions to be reduced, which not only facilitates automation, but which also eliminates the need for subsequent concentration steps which conventionally require the use of a solvent whose presence in the final preparation can adversely effect the quality of the isolated DNA. Thus, the invention offers purification methods which are simple, cost effective, robust and readily amenable to automation.

The present invention also relates to a kit comprising magnetically responsive microparticles having a functional group-coated surface that reversibly binds nucleic acid molecules, at least one binding buffer, a suitable nucleic acid precipitating reagent and salt at concentrations suitable for reversibly binding nucleic acids onto the surface of the microparticle. The kit may additionally comprise preformulated solutions of a host cell lysis buffer, or reagents for the preparation of such buffer, a wash buffer and an elution buffer. The exact compositions of the buffers may vary with the nature of the starting material and the purpose (e.g., the molecular biology application) for which the nucleic acid preparation is being isolated. The kit may further include a magnetic microtiter plate holder specifically designed to optimize the field strength applied to remove the paramagnetic microparticles from the resulting combinations and solutions.

DETAILED DESCRIPTION OF THE INVENTION

As described herein, Applicants have shown that different species of nucleic acid present in a solution can be isolated, on the basis of their molecular size, through the use of appropriate concentrations of a nucleic acid precipitating reagent, preferably a polyalkylene glycol, and a salt to result in the selective precipitation and facilitated adsorption of a particular nucleic acid species to the functional group-coated surfaces of a suitable magnetically responsive solid phase carrier which functions as a bioaffinity adsorbent for a species of nucleic acid molecule targeted for isolation.

According to the instant invention, one embodiment of the method comprises selectively adsorbing (e.g., non-covalently binding) target nucleic acid molecules in a reversible manner to paramagnetic microparticles having a functional group coated (e.g., carboxyl-coated) surface by preparing a combination comprising a mixture of nucleic acid molecules, polyethylene glycol, salt, and solid phase carriers having a functional group-coated surface that reversibly binds nucleic acid molecules wherein the polyethylene glycol and salt are present in sufficient concentrations to selectively precipitate the target species of nucleic acid molecules. The combination (first combination) is maintained under conditions appropriate for adsorption of the precipitated nucleic acid molecules to the functional group-coated surfaces of the solid phase carriers, thereby producing solid phase carriers having the target species of DNA bound thereto. Isolation of the target species of nucleic acid molecules is accomplished by removing the nucleic acid-coated carriers from the first combination. The solid phase carriers (e.g., paramagnetic microparticles) can be recovered from the first combination, for example, by applying a magnetic field to draw down the paramagnetic microparticles. More specifically, paramagnetic microparticles are preferably separated from solutions using magnetic means, such as applying a magnet field of at least 1000 Gauss. However, other methods known to those skilled in the art can be used to remove the magnetic microparticles from the supernatant; for example, vacuum filtration or centrifugation can be used. The remaining solution can then be removed; leaving paramagnetic microparticles having a particular nucleic acid species adsorbed to their surface. Once separated from the mixture, the isolated nucleic acid species adsorbed to the solid phase carrier can be recovered by contacting the microparticles with a suitable elution buffer. As a result, a solution comprising the target nucleic acid molecules and paramagnetic microparticles is produced. Using appropriate means, for example, magnetic means, the microparticles are subsequently removed from the solution whereby the target species of nucleic acid molecule is isolated from the mixture and a second mixture is produced.

A suitable elution buffer can be water or any aqueous solution in which the salt concentration and polyalkylene concentration are below the concentrations required for binding of DNA onto magnetic microparticles, as discussed above. For example, useful buffers include, but are not limited to, TRIS-HCl, Tris-acetate, sucrose (20%) and formamide (100%) solutions. Elution of the DNA from the microparticles occurs quickly (e.g., in thirty seconds or less) when a suitable low ionic strength elution buffer is used. Once the bound DNA has been eluted, the magnetic microparticles are separated from the elution buffer.

Optionally, impurities (e.g., host cell components, proteins, metabolites or cellular debris) can be removed by washing the paramagnetic microparticles with target nucleic acid bound thereto (e.g., by contacting the microparticles with a suitable wash buffer solution) before separating the microparticle-bound nucleic acid from the solid phase magnetically responsive microparticle. The composition of the wash buffer is chosen to ensure that impurities either bound directly to the microparticle, or associated with the adsorbed DNA are dissolved. The pH and solute composition and concentration of the wash buffer can be varied according to the types of impurities which are expected to be present. For example, ethanol exemplifies a preferred wash buffer useful to remove excess PEG and salt. The magnetic microparticles with bound DNA can also be washed with more than one wash buffer solution. The paramagnetic microparticles can be washed as often as required (e.g., three to five times) to remove the desired impurities. However, the number of washings is preferably limited to in order to minimize loss of yield of the bound DNA. A suitable wash buffer solution has several characteristics. First, the wash buffer solution must have a sufficiently high salt concentration (a sufficiently high ionic strength) that the nucleic acid bound to the magnetic microparticles does not elute off of the microparticles, but remains bound. A suitable salt concentrations is greater than about 0.1 M and is preferably about 0.5M. Second, the buffer solution is chosen so that impurities that are bound to the DNA or microparticles are dissolved. The pH and solute composition and concentration of the buffer solution can be varied according to the types of impurities which are expected to be present. Suitable wash solutions include the following: 0.5×5 SSC; 100 mM ammonium sulfate, 400 mM Tris pH 9, 25 mM $MgCl_2$ and 1% bovine serum albumin (BSA); and 0.5M NaCl. A preferred wash buffer solution comprises 25 mM Tris acetate (pH 7.8), 100 mM potassium acetate (KOAc), 10 mM magnesium acetate ($Mg_2OAc$), and 1 mM dithiothreital (DTT).

In an alternative embodiment the method provides a method of selectively isolating an additional species of nucleic acid molecules from the second mixture (produced by the removal of nucleic acid-coated microparticles from the first combination) wherein the additional species of nucleic acid molecule is of a smaller molecular size than the first target species isolated from the first combination. More specifically, this method comprises the steps of producing a second combination by adding to the second mixture solid phase carriers having a functional group-coated surface that reversibly binds nucleic acid molecules, polyethylene glycol and salt, wherein the polyethylene glycol and salt are present in sufficient concentrations to precipitate the additional target species of nucleic acid molecules. The second combination is maintained under conditions appropriate for the absorption of the additional target species to the functional group-coated surfaces of the solid phase carries, thereby producing solid phase carriers having the additional target species of nucleic acid molecule bound thereto. Isolation is accomplished by removing the solid phase carriers having the additional species of nucleic acid molecules absorbed thereto from the second combination and eluting the additional target species into a suitable low ionic strength solution.

As used herein the terms "nucleic acid" and "nucleic acid molecule" are used synonymously with the term polynucleotides and they are meant to encompass DNA (single-stranded, double-stranded, covalently closed, and relaxed circular forms), RNA (single-stranded and double-stranded), RNA/DNA hybrids and polyamide nucleic acids (PNAs).

The term "species" as it used herein to refer to nucleic acid molecules means a particular subclass, family or type of nucleic acid molecule defined on the basis of a characteristic size. Thus, the members of a "species of nucleic acid molecules" are all of approximately equivalent molecular size within a small range of molecule sizes.

As used herein the term "isolated" is intended to mean that the material in question exists in a physical milieu distinct from that in which it occurs in nature and/or has been completely or partially separated or purified from other nucleic acid molecules.

Appropriate starting material includes, but is not limited to, lysates prepared from cells obtained from either mammalian tissue or body fluids, nucleic acid samples eluted from agarose or polyacrylamide gels, solutions containing multiple species of DNA molecules resulting either from a poymerase chain reaction (PCR) amplification or from a DNA size selection procedure and solutions resulting from a post-sequencing reaction. Suitable starting solutions typically are mixtures of biomolecules (e.g. proteins, polysacchardies, lipids, low molecular weight enzyme inhibitors, oligonucleotides, primers, templates) and other substances such as agarose, polyacrylamide, trace metals and organic solvents, from which the target nucleic acid molecule must be isolated.

For example, a suitable starting material can be host cells containing an exogenous nucleic acid (e.g., recombinant DNA, bacterial DNA or replicative form DNA) which is targeted for isolation from host cell chromosomal DNA and other host cell biomolecules. According to the current method, host cells are lysed using known methods, thereby preparing a mixture suitable for use with the method of the instant invention. An alternative starting material appropriate for use with the current invention is an agarose solution. For example, a mixture of nucleic acid can be separated, according to methods known to one skilled in the art (e.g., gel electrophoresis), such as by agarose gel electrophoresis. A plug of agarose containing nucleic acid on interest can be excised from gel and combined with an appropriate buffer, into which the nucleic acid is released by heating the combination to dissolve the agarose plug. The method of the instant invention can also be used to separate a particular species of DNA present in a post-shearing procedure mixture; or to remove a template and primers from a sequencing reaction or to separate PCR primers from the reaction product of a PCR amplification protocol.

As used herein the terms "selective" and "selectively" refer to the ability to isolate a particular species of DNA molecule, on the basis of molecular size (e.g., host cell chromosomal DNA or exogenous plasmid DNA), from a combination which includes or is a mixture of species of DNA molecules, such as a host cell lysate and other host cell components. The selective isolation of a particular species is accomplished through the use of an appropriate precipitating reagent (e.g., polyalkylene glycol salt) to result in the precipitation and facilitated adsorption of a,.particular DNA species (e.g., characterized on the basis of size) to the surfaces of paramagnetic microparticles.

Suitable precipitating reagents include ethanol, isopropanol and polyalkylene glycols. Appropriate polyalkylene glycols include polyethylene glycol (PEG) and polypropylene glycol. Generally, PEG is used. Suitable PEG can be obtained from Sigma (Sigma Chemical Co., St. Louis, Mo., Molecular weight 8000, Dnase and Rnase fee, Catalog number 25322-68-3) The molecular weight of the polyethylene glycol (PEG) can range from about 6000 to about 10,000, from about 6000 to about 8000, from about 7000 to about 9000, from about 8000 to about 10,000. In a particular embodiment PEG with a molecular weight of about 8000 is used. In general, the presence of PEG provides a hydrophobic solution which forces hydrophilic nucleic acid molecules out of soltution. The advantages of using PEG which is a nondenaturing water soluble polymer, rather than an organic precipitating reagent (e.g., ethanol, isoproponal or phenol), are attributed to its benign chemical properties. According to the current invention, the PEG-induced nucleic acid precipitates are adsorbed to the surfaces of magnetically responsive microparticles which can be physically manipulated to facilitate the isolation of essentially pure species of nucleic acid molecules from complex solutions comprising mixtures of nucleic acids, in the presence or absence of other host cell biomolecules. Although numerous biological macrostructures (bacteriophage, ribosomes, plant and animal viruses, proteins and nucleic acids) are precipitable with PEG, the threshold concentration required varies for each macrostructure (Lis, Methods in Enzymology, 1980). This observation makes it possible to use the instant method to isolate nucleic acid molecules, not only from other nucleic acid molecules having a different molecular size, but also from other host cell biomolecules and biological macrostructures, each of which will have a distinct PEG threshold concentration at which it will precipitate.

Suitable salts which are useful for facilitating the adsorption of nucleic acid molecules targeted for isolation to the magnetically responsive microparticles include sodium chloride (NaCl), lithium chloride (LiCl), barium chloride ($BaCl_2$), potassium (KCl), calcium chloride ($CaCl_2$), magnesium chloride ($MgCl_2$) and cesium chloride (CsCl). In a preferred embodiment, sodium chloride is used. In general, the presence of salt functions to minimize the negative charge repulsion of the nucleic acid molecules. The wide range of salts suitable for use in the method indicates that many other salts can also be used and suitable levels can be empirically determined by one of ordinary skill in the art.

As used herein, "facilitated adsorption" refers to a process whereby a precipitating reagent, (e.g., a poly-alkyelene glycol) is used to promote the precipitation and subsequent adsorption of a species of DNA molecules, which were initially in mixture, onto the surface of a solid phase carrier.

The resulting reversible interaction is distinct from, for example, an interaction between two binding partners (e.g., streptavidin/biotin, antibody/antigen or a sequence-specific interaction), which are conventionally utilized for the purpose of isolating particular biomolecules based on their composition or sequence.

Suitable magnetically responsive paramagnetic microparticles have sufficient surface area to permit efficient binding and are further characterized by having surfaces which are capable of reversibly binding nucleic acids. Suitable solid phase carriers include, but are not limited to, other particles, fibers, beads and or supports which have an affinity for DNA and which can embody a variety of shapes, that are either regular or irregular in form, provided that the shape maximizes the surface area of the solid phase, and embodies a carrier which is amenable to microscale manipulations. Generally, paramagnetic microparticles are used.

As used herein, "paramagnetic microparticles" refers to microparticles which respond to an external magnetic field (e.g., a plastic tube or a microtiter plate holder with an embedded rare earth (e.g., neodymium) magnet but which demagnetize when the field is removed. Thus, the paramagnetic microparticles are efficiently separated from a solution using a magnet, but can be easily resuspended without magnetically induced aggregation occurring. Preferred paramagnetic microparticles comprise a magnetite rich core encapsulated by a pure polymer shell. Suitable paramagnetic microparticles comprise about 20–35% magnetite/encapsulation ratio. For example, magnetic particles comprising a magnetite/encapsidation ration of about 23%, 25%, 28% 30% 32% or 34% are suitable for use in the present invention. Magnetic particles comprising less than about a 20% ratio are only weakly attracted to the magnets used to accomplish magnetic separations. Depending on the nature of the host cell, the viscosity of the cell growth and the nature of the vector (e.g. high or low copy) paramagnetic microparticles comprising a higher percentage of magnite should be considered. The use of encapsulated paramagnetic microparticles, having no exposed iron, or $Fe_3O_4$ on their surfaces, eliminates the possibility of iron interfering with polymerase function in certain downstream manipulations of the isolated DNA. However the larger the magnetite core the higher the chance of encapsulation leakage (e.g., release of iron oxides). Suitable paramagnetic microparticles for use in the instant invention can be obtained for example from Bangs Laboratories Inc., Fishers, Ind. (e.g., estapor® carboxylate-modified encapsulated magnetic microspheres).

Suitable paramagnetic microparticles should be of a size that their separation from solution, for example by magnetic means or by filtration, is not difficult. In addition, preferred paramagnetic microparticles should not be so large that their surface area is minimized or that they are not suitable for microscale manipulation. Suitable sizes range from about 0.1 $\mu$ mean diameter to about 100 $\mu$ mean diameter. A preferred size is about 1.0 $\mu$ mean diameter.

As used herein, the term "functional group-coated surface" refers to a surface which is coated with moieties which reversibly bind nucleic acid (e.g., DNA, RNA or polyamide nucleic acids (PNA)). One example is a surface which is coated with moieties which each have a free functional group which is bound to the amino group of the amino silane or the microparticle; as a result, the surfaces of the microparticles are coated with the functional group containing moieties. The functional group acts as a bioaffinity adsorbent for polyalkylene glycol precipitated DNA. In one embodiment, the functional group is a carboxylic acid. A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the paramagnetic microparticle. Suitable solid phase carriers having a functional group coated surface that reversibly binds nucleic acid molecules are for example, magnetically responsive solid phase carriers having a functional group-coated surface, such as, but not limited to, amino-coated, carboxyl-coated and encapsulated carboxyl group-coated paramagnetic microparticles.

One embodiment of the instant invention is a method of selectively isolating a target species of nucleic acid molecule, on the basis of its molecular size, from a solution comprising a mixture of the target nucleic acid species in the presence or absence of other species of nucleic acid molecules and other biomolecules. As described herein, the method comprises preparing a combination comprising a mixture of nucleic acids in the presence of polyethylene glycol (PEG) and salt, wherein the PEG and salt concentrations are sufficient to selectively precipitate a particular species of nucleic acid molecule, which has been targeted for isolation. The PEG and salt should be present at levels which are sufficient to precipitate the targeted nucleic acid species, but insufficient to precipitate relatively smaller sized nucleic acid molecules or other host cell biomolecules. The precipitated nucleic acid species targeted for isolation is removed from the solution by adding a solid phase carrier, such as a magnetically responsive microparticle, which has a functional group-coated surface that reversibly binds nucleic acid molecules to its surfaces. The nucleic acid-coated carrier represents a solid phase product which can subsequently be removed from the starting solution by the application of an external force (e.g., centrifugation, filtration or magnetic field).

The removal of the solid phase microparticle from the solution, results in the isolation of a target species of nucleic acid molecule, characterized by a particular molecular size, which is essentially free of other host cell biomolecules and as a consequence produces a solution from which nucleic acids characterized by a particular molecular size have been removed. An additional species of nucleic acid molecule (e.g., a second, third, fourth, etc.) characterized by having a relatively smaller molecular size can subsequently be isolated from the resulting solution by adding solid phase carriers, having a functional group-coated surface that reversibly binds nucleic acid molecules, to the solution (from which nucleic acid molecules of relatively higher molecular weight have been removed) in the presence of sufficient polyethylene glycol and salt to precipitate the relatively smaller species of nucleic acid molecule subsequently targeted for isolation. The resulting combination is maintained under conditions which favor the adsorption of the second nucleic acid species, but not other host cell biomolecules present in the solution, to the surfaces of the microparticles, thereby producing a second solid phase product. The removal of the second solid phase product from the solution results in the isolation of an additional species of nucleic acid molecule that is essentially free of other species of nucleic acid molecules, characterized by different molecular sizes, and of other biomolecules present in the starting solution.

As used herein a "host cell" is any cell into which exogenous DNA can be introduced, producing a host cell which contains exogenous DNA, in addition to host cell DNA. As used herein the terms "host cell DNA" and "endogenous DNA" refer to DNA species (e.g., genomic or chromosomal DNA) that are present in a host cell as the cell is obtained. As used herein, the term "exogenous" refers to DNA other than host cell DNA; exogenous DNA can be present into a host cell as a result of being introduced in the host cell or being introduced into an ancestor of the host cell. Thus, for example, a DNA species which is exogenous to a particular host cell is a DNA species which is non-endogenous (not present in the host cell as it was obtained or an ancestor of the host cell). Appropriate host cell include, but are not limited to, bacterial cells, yeast cells, plant cells and mammalian cells.

The term "lysed host cell suspension", as used herein, refers to a suspension comprising host cells whose membranes have been disrupted by any means (e.g., chemical, such as alkali or alkali and anionic detergent treatment, isotonic shock, or physical disruption by homogenization), such a suspension is a mixture of host cell biomolecules, cellular components and disrupted membrane debris. In one embodiment, a lysed host cell suspension suitable for use in the instant invention is prepared by contacting host cells with an alkali and anionic detergent (e.g., sodium dodecyl sulphate (SDS)) solution (e.g., 0.2 N NaOH, 1% SDS). Optionally, lysozyme could be included in the lysis buffer. The presence of an anionic detergent in the lysing solution functions to produce an anti-protein environment by neutralizing the effective charge of the proteins, thereby minimizing their attraction to the surfaces of the functional group-coated paramagnetic microparticles. In one embodiment, the lysed host cell suspension is non-neutralized. Optionally, RNase can be added to the host cell lysate to degrade host cell RNA, thereby allowing DNA to bind to the magnetic microparticles free, or essentially free, from RNA. The necessity of including a Rnase step will largely be determined by the size of the nucleic acid species that is targeted for isolation in the particular PEG-induced precipitation that is being performed. For example, if the conditions selected for isolation are appropriate for isolating nucleic acids comprising at least 4000 base pairs, then it is unlikely that RNA species will be an appreciable contaminant.

In one embodiment, the present invention provides a method of selectively isolating a species of nucleic acid molecule present in a mixture from other nucleic acid molecules, and from other biomolecules, biological macrostructures, or reagents possibly present in the starting material. More specifically, this embodiment of the method involves: combining a mixture which comprises the target species of nucleic acid molecules to be isolated admixed with other nucleic acid molecules, biomolecules, biological macrostructures or reagents; solid-phase carriers (e.g., particles) having a functional group-coated surface, which acts as a bioaffinity absorbent for nucleic acids; a suitable concentration of a nucleic acid precipitating reagent(s) (e.g., polyethylene glycol (PEG) and salt, or an alcohol, such as ethanol or isopropanol) to result in the facilitated absorption of the target species of nucleic acid molecules, but not of smaller-sized species of nucleic acid molecules or other biomolecules, biological macrostructures or reagents present in the starting material. Separation of the target species of nucleic acid molecule is accomplished by applying an external force (e.g., magnetic field, centrifigation, filtration) suitable to remove the solid phase carrier having the selectively precipitated nucleic acid bound thereto from the combination. In a preferred embodiment the solid phase carrier is a paramagnetic microparticle and separation is accomplished by applying a magnetic field of appropriate strength. In a further embodiment the solid phase carrier is a paramagnetic microparticle and separation is accomplished by applying a magnetic field of at least 1000 Gauss. This embodiment of the invention is useful for example to isolate a restriction enzyme digest fragment having a particular molecular size from smaller fragments present in the same digest; for isolating a single PCR product from a multiplex PCR reaction; for the selection of DNA fragments having a homogenous sized distribution resulting from a shearing procedure (e.g., nebulizer, sonicator, hydroshear); for removing a nucleic acid template from a sequencing reaction or for selectively precipitating the extension products (e.g., Sanger Sequencing products) from a detemplated sequencing reaction prior to capillary electrophoresis. For example, the production of shattered DNA libraries for large scale sequencing experiments requires a size-selection step to minimize the deviation in size of the DNA inserts selected for cloning. The ability to produce a library comprising sheared DNA fragments, characterized by a narrow size distribution improves an investigator's ability to construct a map of the original pre-sheared DNA molecule. Using the method described herein an investigator can preselect a cut off size and formulate a binding buffer appropriate to precipitate and selectively adsorb a homogeneous population of DNA fragments. This embodiment can also be used to isolate extension products from a detemplated sequencing reaction mixture. The adsorbed nucleic acid molecules (e.g., Sanger sequencing products) can be thoroughly washed free of salts (e.g., reagent) and excess terminals whose presence will interfere with the electrophoretic injection of the sample to be sequenced.

In a second embodiment, the method disclosed herein can be used to isolate two different species, for example, endogenous host cell nucleic acids and exogenous nucleic acid molecules, present in the starting material, by first isolating the relatively higher molecular weight host cell DNA, and subsequently isolating the relatively smaller-sized exogenous nucleic acid molecules. Thus, an alternative embodiment of the instant invention further provides a means for the selective removal of endogenous host cell DNA from a lysed host cell suspension by performing a first step designed to precipitate and promote the adsorption of host cell DNA chromosomal to the functional group-coated surfaces (e.g., a carboxyl-group-coated surface) of a suitable solid phase carrier (e.g., microparticle surfaces). The removal of the solid phase carrier (to which the host cell DNA is bound) from the resulting mixture results in the removal of the relatively larger-sized host cell DNA.

As described above, high quality exogenous DNA can subsequently be isolated from an exogenous DNA enriched supernatant by selectively precipitating and adsorbing the relatively lower molecular weight exogenous DNA to the surfaces of additional paramagnetic microparticles which are introduced resulting into the supernatant.

This alternative embodiment, which results in isolation of both endogenous host cell nucleic acid and exogenous nucleic acid (separately) comprises: combining functional group-coated paramagnetic microparticles and suitable concentrations of a precipitating reagent, for example, a polyalkylene glycol, and a salt to promote the facilitated adsorption of precipitated endogenous host cell nucleic acid (e.g., chromosomal DNA) and subsequently of exogenous nucleic acid molecules (e.g., bacterial or viral nucleic acids), each species being characterized by a particular molecular size, to the surfaces of the microparticles suspended therein; and the removal, such as by magnetic means, of the nucleic acid-coated microparticles from the resulting first combination. The removal of the microparticle having endogenous host cell nucleic acid adsorbed to its surfaces from the first combination results in the concomitant separation of host cell nucleic acid from both exogenous nucleic acid species and from other host cell biomolecules present in the sample. Exogenous nucleic acid present in the same sample can subsequently be isolated by producing a second combination by adding paramagnetic microparticles which have a functional group-coated surface and a sufficient quantity of a nucleic acid precipitating reagent to increase the concentration of the precipitating reagent to a level sufficient to result in the adsorption of exogenous nucleic acid to the microparticles suspended therein, thereby producing a third combination comprising exogenous nucleic acid bound to the microparticles; removing the paramagnetic microparticles from the third combination. Thus, exogenous nucleic acid bound to the microparticles is isolated from other host cell biomolecules present in the starting solution. Thus, the present invention also provides a method of selectively separating exogenous nucleic acids from relatively larger species of endogenous host cell nucleic acids present in the same sample.

The selective precipitation of endogenous host cell DNA (e.g., chromosomal or genomic DNA is mediated by concentrations of PEG as low as about 1% (w/v) and as high as about 4% (w/v) depending upon the size of the host cell DNA and the ionic strength of the solution. In a preferred embodiment, the concentration of PEG is preferably adjusted to about 3% (weight/volume). The subsequent selective precipitation of exogenous plasmid DNA is accomplished by adjusting the PEG concentration to a level which has been empirically determined to be optimal to promote the precipitation of a DNA species of a specified macromolecular size range. For example, exogenous DNA produced from the replication of a bacterial plasmid in a suitable strain of $E.$ $coli$ would be isolated by adjusting the PEG concentration of the second precipitation reaction to about 10% (weight/volume).

At high salt concentrations (e.g., synonymous with high ionic strengths) suitable paramagnetic microparticles will adsorb DNA fragments of all sizes. The term "high salt concentration" refers to salt concentrations greater than about 0.5M. At "low salt concentrations" (or low ionic strengths), which as used herein connotes concentrations less than about 0.2 M, essentially no DNA, of any size, will be precipitated even in the presence of a PEG concentration that is as high as 12% (weight/volume) (Lis, John T, $Methods$ $in$ $Enzymology$ 65: 437–353 (1980). At intermediate salt concentrations (e.g., ranging from about 0.3M to about 0.45M) the characteristic macromolecular size of the DNA species precipitated by a particular PEG concentration is a function of the interaction between ionic strength and PEG concentration and reflects a relationship between macromolecular size and requisite threshold PEG concentration required to precipitate DNA molecules of a given size. In general, smaller fragments of DNA will interact with the functional group-coated surfaces with a lower affinity than larger DNA fragments in the presence of relatively low concentrations of salt. To maximize yield and efficiency, sodium chloride concentration is preferably adjusted to about 0.55 M for the selective removal of host cell DNA from a lysed host cell suspension. Yields of bound DNA decrease if the salt concentration is adjusted to less than about 0.5 M or greater than about 5.0 M. Purity (e.g. quality) of recombinant DNA isolated during the second precipitation reaction decreases if the sodium chloride concentration exceeds about 0.55 M.

Another embodiment of the instant invention provides a method by which recombinant nucleic acid molecules expressed in host cells can be selectively isolated from host cell lysates comprising a mixture of nucleic acid molecules and other host cell biomolecules. The following is a description of this embodiment with reference to nucleic acid molecules as exemplified by DNA. It is to be understood that the instant embodiment is also useful for separation of other nucleic acids in a similar manner. This embodiment of the invention comprises the steps of: preparing a first combination comprising a lysed host cell solution prepared from cells expressing a recombinant nucleic acid; encapsulated carboxyl group-coated paramagnetic microparticles, and low percentage PEG and low molarity salt. According to the method disclosed herein, the PEG and salt are present at sufficient concentrations that high molecular weight host cell DNA is precipitated and reversibly binds (adsorbs) to the encapsulated carboxyl group-coated paramagnetic microparticles, thereby producing paramagnetic microparticles having host cell DNA bound thereto. The DNA-coated microparticles (and, thus, the microparticle-adsorbed endogenous DNA) are removed from the first combination, thereby producing a recombinant DNA-enriched supernatant. A second combination is produced by adding carboxyl group-coated paramagnetic microparticles to the recombinant DNA-enriched supernatant and sufficient polyethyleme glycol to result in the selective precipitation and adsorption of the relatively smaller sized recombinant DNA to the surfaces of the micro-particles, thereby producing paramagnetic microparticles having recombinant DNA bound thereto; and removing the paramagnetic microparticles (and thus, the adsorbed recombinant DNA), whereby recombinant DNA is selectively isolated from host cell DNA.

Examples of recombinant DNA which can be introduced into a host cell include, but are not limited to, bacterial artificial chromosomes (BACs), yeast artificial chromosomes (YACs), PACs, P1s, cosmids and bacterial plasmids. The exogenous DNA may be directly introduced into a host cell, or an ancestor thereof, by means well known to one of ordinary skill in the art, such as transformation or transfection methods. Alternatively, plasmid DNA may be indirectly introduced into a host cell, or its ancestor by use of a phage into which exogenous DNA has been packaged. Suitable plasmid DNAs which can be packaged into a phage include a cosmid or P1 vector. Suitable host cells include bacterial cells, yeast cells, plant cells and mammalian cells. For example, suitable strains of $E.$ $coli$ bacteria include but are not limited to: DH5α, DH1, DH10B, DH12S, C600 or XL-1 Blue. As used herein the term "plasmid" refers to double stranded circular DNA species which originate from an exogenous source (e.g., are introduced into a host cell) and which are capable of self-replication independent of host chromosomal DNA. Thus, the term encompasses cloned DNA produced from the replication of any of the above-mentioned vectors. Suitable vectors are well known in the art and include, for example high copy vectors, selected from, but not limited to the group consisting of pUC, pOT, pBluescript, pGEM, pTZ, pBR322, pSC11, pACYC, Super-Cos and pWE15.

BACs are particularly difficult to separate and purify from cleared lysates due to their low concentrations in the lysates, which is attributable to their low copy number presence in the host cell. However, BAC DNA (e.g., up to 180 kb in size) is readily isolated by the method of the present invention. Cosmids are particularly difficult to isolate from expression host cells using commercially available chromatography-based methods because of their relatively large size (e.g., 35 to 40 kb). However, cosmids are readily separated by the methods of the present invention.

Thus, the method of the present invention is also useful to separate recombinant DNA resulting from the replication of an exogenous vector from a host cell lysate containing an admixture of host cell biomolecules, including host cell DNA and exogenous cloned DNA produced by the host cell. Yields of recombinant DNA following elution typically approach 100% when the magnetic microparticles are used in excess. High copy plasmid DNA templates have been prepared according to the disclosed method characteristically result in sequences which were read with 99% of unedited accuracy. The simplicity and robust nature of the disclosed method makes it particularly useful for the preparation of DNA sequencing templates for automated nucleotide sequencing.

Another embodiment of the present invention relates to a method of isolating a nucleic acid molecule suitable for use as a template for nucleotide sequencing using either manual or high-throughput automated sequencing methods. This embodiment comprises: treating host cells with an alkali and anionic detergent combination, thereby producing a lysed host cell suspension; suspending paramagnetic microparticles which bind DNA in the lysed host cell suspension in the presence of low percentage polyethylene glycol and low molarity salt, which promotes the precipitation and selective adsorption of host cell DNA to the surfaces of the microparticles; removing the paramagnetic microparticles having host cell DNA bound thereto from the suspension, thereby producing a plasmid-enriched supernatant; combining additional paramagnetic microparticles which bind DNA with the plasmid-enriched supernatant and adjusting the polyethylene glycol percentage and salt concentration of the supernatant to levels which result in binding of plasmid DNA to the microparticles; removing the microparticles having plasmid DNA bound thereto from the supernatant; washing the microparticles with a wash buffer to remove impurities adsorbed to the microparticles, thereby producing a purified template; and contacting the microparticle-bound purified template with an elution buffer, whereby the plasmid DNA template is released from the microparticles and is dissolved in the elution buffer, thereby isolating a purified plasmid DNA template suitable for nucleotide sequencing.

The present invention also further relates to a kit comprising reagents for preparing a host cell lysate which is appropriate for automated processing according to a system which has been optimized for high through-put DNA templates preparation; and an aqueous solution of paramagnetic microparticles having a functional group-coated surface capable of reversibly binding nucleic acid molecules. In addition the kit may comprise either at least one binding preformulated binding buffer comprising polyalkylene glycol and salt, at concentrations which been empirically determined to be appropriate to reversibly bind nucleic acid molecules characterized by a particular molecular size range onto the functional group-coated surfaces of the paramagnetic microparticles, or reagents for the formulation of a binding buffer. Additionally, the kit may comprise at least one preformulated high ionic strength buffer suitable for use as a wash buffer, or reagents for preparing such buffer; a preformulated elution buffer or reagents for its preparation; and a magnetic microtiter plate holder designed to optimize features of the magnetic field known to be crucial to the efficiency of automated processing. The design of the magnetic plate holder is instrumental in producing a magnetic field having the requisite uniformity and field strength to maximize the efficiency achievable with automatic processing. Field Strength of up to and over 1600 Gauss can be achieved with the use of N35 rare earth magnets configured with alternating North and South polar spaced 9 mm apart. Since the magnetically responsive microparticles are paramagnetic they will attract to either pole.

The isolation of high quality nucleic acid preparations from starting solutions of diverse composition and complexity is a fundamental technique in molecular biology. Thus, as a result of the work described herein, novel and readily automatable methods of isolating and purifying nucleic acid molecules are now available. Nucleic acids isolated by the disclosed method can be used for molecular biology applications requiring high quality nucleic acids, for example, the preparation of DNA sequencing templates, the microinjection, transfection or transformation of mammalian cells, the in vitro synthesis of RNA probes, reverse transcription cloning, cDNA library construction, PCR amplification, or gene therapy research, as well as for other applications with less stringent quality requirements including, but not limited to, transformation, restriction endonuclease or microarray analysis, selective RNA precipitations, in vitro transposition, separation of multiplex PCR amplification products, preparation of DNA probes and primers and detemplating protocols.

The following Examples are offered for the purpose of illustrating the present invention and are not to be construed to limit the scope of this invention. The teachings of all references cited herein are hereby incorporated, in their entirety, by reference.

GENERAL METHODOLOGY

Beads

The paramagnetic microparticles used in the following examples were polymer p (S/V-COOH)Mag/Encapsulated paramagnetic microspheres (brown, mean diameter 1.12 $\mu$m, 10% solids; catalog number ME03N) from Bangs Laboratories, Inc., (Fishers, Ind.). The particles were stored in phosphate buffered saline (PBS) at a concentration of 20 mg/ml.

Bead Pretreatment

Prior to use in any of the separation protocols exemplified herein, all beads are washed four times with 10 mM Tris Acetate pH 7.8, and diluted tenfold in the 10 mM Tris Acetate buffer. More specifically, all beads are washed and diluted according to the following protocol:

1. Place 4 mls of beads into a tube.
2. Add 26 mls of 10 mM Tris Acetate.
3. Apply a magnet to the suspension, and pour off the wash buffer.
4. Repeat steps 2–3, 3 times.
5. Resuspend the washed beads in a final volume of 40 mls of 10 mM Tris Acetate.

Lysis Buffer Preparation

Prepare 0.8 N NaOH/8% SDS lysis buffer by combining 160 ml of 2 N NaOH, 160 mls of 20% SDS, and 80 mls of distilled water. Immediately after mixing the buffer should be warmed to, and maintained at a temperature of 60–70 degrees C. Lysis buffer should be prepared fresh daily.

Sample Preparation

Pellet cells (e.g., centrifuge at 1645×g, for 10 mins.); decant culture medium; resuspend the pelleted cells in water in a final volume that is appropriate based on the density of the starting culture; vortex (e.g., 1200 rpm for 6 mins); and transfer an aliquot of the resulting cell suspension to flat bottom multiwell plates (e.g., 150 $\mu$l in a 96-well plate).

Ethanol Wash Protocol

The paramagnetic microparticle bound nucleic acid species is washed free of contaminants using three to five sequential washes with 70% Ethanol, with the volume transfers either being accomplished by hand or by using an automated plate washer (e.g., Tecan SLT/PW). A suitable wash protocol using an automated plate washer would consist of the three to five repetitions of the following cycle: add 250 ul ethanol, soak for 20 seconds, aspirate for 7 seconds and repeat.

Sequencing

Suitable automated sequencing reactions can be performed using Amersham ET primer Thermosequence 2 terminator chemistry, Big Dye primer and terminator chemistries, NEN/Omnibase terminator chemistries, or AB1 FS terminator chemistry using established protocols that are well known to those of skill in the art. Sequence results can be obtained using AB1377 Sequencers, MD MegaBACE capillary or ABI 3700 capillary sequencers. All agarose gels were run using 1% final agarose (U.S. Biochemical #32827) with 1×TBE buffers. The field strength was 10 V/cm with run times from 40–60 minutes. The gels were post-stained with ethidium bromide and visualized under UV.

EXAMPLE 1

Isolation of Plasmid DNA Using PEG-Induced Separation and Paramagnetic Microparticles This example provides a procedure, using the method described herein, to simultaneously process 96 individual plasmid miniprep samples from bacterial host cells comprising a pOT plasmid. The teaching of the instant disclosure provides ample guidance to allow an investigator of ordinary skill to modify this example to perform routing experimentation to derive a modification of this method that is capable of isolating exogenous DNA produced by the expression of alternative vectors (e.g., cosmids, BACs, P1s etc), in either high-copy- or low-copy-number, in numerous alternative host cells. Plasmid (e.g., exogenous) DNA was purified from the host cells by producing a mixture host cell lysate; preclearing the lysate of high molecular weight endogenous (e.g., host cell genomic) DNA by selectively precipitating it under conditions which promote its adsorption, but not the adsorption of pOT plasmid DNA, to paramagnetic microparticles; removing the endogenous DNA-coated microparticles from the sample; transferring the resulting exogenous DNA (e.g., plasmid DNA) enriched solution to new microtiter wells; selectively precipitating the plasmid DNA to additional paramagnetic microparticles; removing the plasmid DNA coated microparticles from the sample; and eluting the purified pOT exogenous DNA from the microparticles. The following procedure was used:

1. Produce a host cell lysate.
    Place 1.2 ml aliquots of an overnight culture of *E. coli* host cells comprising the pOT plasmid into each well of a 96 deep well microtiter plate.
    Centrifuge the plate for 5 minutes to pellet the host cells.
    Pour off, or aspirate, the resulting supernatant and resuspend the host cell pellet in a 150 µl volume of Tris-Acetate (pH 7.8), or in an alternative volume appropriate for the capacity of the wells of the assay plate being used for processing of the miniprep samples.
    Transfer the resulting host cell 150 µl host cell suspension to the corresponding wells of a 96 shallow well microtiter plate.
    Add 50 µl of freshly prepared and prewarmed Lysis Buffer (0.8 N NaOH, 4% SDS) and mix by shaking.
2. Removal of High Molecular Weight Endogenous DNA
    Add 20 µl of prewashed carboxyl-coated paramagnetic microparticles to the host cell lysate mixture.
    Add 55 µl of Precipitation Buffer (18% PEG 8000, 3.3 M NaCl) and mix by shaking.
    Remove the high molecular DNA-coated microparticles from the sample, preferably by magnetic means; thereby producing a lysate which is precleared of high molecular weight DNA and enriched for exogenous plasmid DNA.
3. Selective Isolation of Plasmid DNA
    Transfer 210 µl aliquots of the resulting plasmid DNA-enriched solution to new wells of a second shallow well microtiter plate.
    Add 20 µl of prewashed carboxyl-coated paramagnetic microparticles to the host cell lysate mixture.
    Add 45 µl of Binding Buffer (40% PEG 8000) and mix by shaking.
    Remove the plasmid-DNA coated paramagnetic microparticles from the sample and discard the supernatant. For example, suitable magnetic means for the removal of the microparticles comprise exposing the microtiter sample plate to a magnetic field of about 1000 Gauss.
    Wash the plasmid DNA coated microparticles three to four times with 250 µl volumes of Wash Buffer (70% Ethanol, 10 mM EDTA or 12% Pyrilidinone).
    Air dry the washed microparticles.
    Elute the purified plasmid DNA from the microparticle by resuspending the washed microparticles in a small volume (e.g., 40 µl) of a low ionic strength Elution Buffer, such as water or 10 mM Tris (pH 7.8).

Results

Electrophoresis: Electrophoretic analysis of the nucleic acid eluted from the paramagnetic microparticles used to adsorb the high molecular weight endogenous DNA indicates the presence of genomic DNA and no RNA or exogenous plasmid DNA. Electrophoretic analysis of the supernatant produced by the removal of the endogenous DNA-coated microparticles reveals the presence of RNA and relatively smaller molecular weight plasmid DNA. Electrophoretic analysis of the nucleic acids eluted from the plasmid DNA-coated microparticles obtained in the step (3), indicates purified plasmid DNA in the absence of any other detectable nucleic acids. Yields typically range from 10–20 µgs per 1.2 ml of host cell culture.

Sequencing: Plasmid DNA isolated according to the procedure described in this example was sequenced using Taq FS polymerase and fluorescently labeled terminators. The DNA sequence was then electrophoresed on an ABI 3700 sequencer. The clarity of the data, the low frequency of ambiguous bases and the average read length evidence DNA of high purity.

This example demonstrates that DNA obtained using the method described herein is suitable for use in both manual and automated nucleotide sequencing protocols; including methodologies which employ cycle sequencing chemistries enabled by the use of DNA polymerases having improved thermostability.

EXAMPLE 2

PEG-Induced Size Selection of Sheared DNA for Shotgun Library Construction

Shortgun sequencing strategies enable the de novo determination of an unknown nucleotide sequence. The method imposes no limitation on the size of the starting DNA molecule whose sequence is to be determined and requires no prior knowledge of the nucleotide sequence of the DNA fragments selected as inserts for cloning. According to protocols which are well-known to those of skill in the art, the starting DNA molecule, whose sequence is to elucidated, s fragmented, either by enzymatic digestion or by physical shearing (e.g., using a nebulizer, sonicator or hydroshearing) to produce a shattered DNA library typically comprising 0.5–5 kb fragments. The shotgun strategy then requires that a subfraction of these fragments characterized by a narrow size range (e.g., 0.5–1.0 kb, 0.8–1.5 kb, 1.0–1.5 kb) be selected for use as inserts into an appropriate DNA sequencing vector. The nucleotide sequences of the resulting subclones are subsequently determined from standard primer binding sites present in the flanking DNA of conventional sequencing vectors. The ability to selectively isolate high purity subfractions comprising DNA fragments characterized by a narrow size range facilitates the construction of a ungapped map comprising the complete sequence of the starting DNA molecule which results from assembling the resulting subclone sequences into contigs. As shown in this example the method described herein enables an investigator of ordinary skill to selectively precipitate DNA fragments characterized by a narrow size range. Successful practice of the embodiment of the invention requires only routine experimentation to empirically determine the composition of a suitable binding buffer which results in the precipitation of a population of subclones characterized by a size range selected by the investigator. For example, an investigator can chose to isolate all fragments larger than a single cut off size which is determined by the percentage of PEG and molarity of salt used to prepare the binding buffer. Alternatively, an investigator may employ sequential PEG-Induced precipitations, according to the method provided herein, to isolate fragments characterized by a narrow size range defined by two different molecular size cut offs which differ from each other by at least a factor of two. For example, the following protocol has been used to select fragments of sheared BAC DNA for subcloning:

1. Prepare a Shattered Fragment Library of the DNA to be sequenced.
    Place 5–10 $\mu$g of BAC DNA suspended in 200 $\mu$l of water and shatter by hydrodymic shearing using a HydroShearm™(Genemachines) at speed 10.
2. Isolation of DNA Fragments Characterized by a Narrow Size Range Using PEG-Induced Size Selection
    Add 20 $\mu$l of prewashed carboxyl-coated paramagnetic microparticles to
    a 100 $\mu$l aliquot of sheared DNA mixture.
    Add 110 $\mu$l of a Selective Binding Buffer formulated to precipitate and facilitate the adsorption of DNA fragments larger than a particular size, and mix by shaking. The composition of an appropriate Binding Buffer should be empirically determined based on preliminary experiments performed using Binding Buffers of varying compositions of PEG and salt, combined with electrophoretic analysis of the precipitated nucleic acids. The size range of the desired fragments selected for precipitation will be dependent on the length of the starting DNA sequence that is being elucidated and the expected average read length of the subcloned sequences. For example, a binding buffer comprising 18% PEG and 0.6 M NaCl can be used to isolate fragments having the size range of 1.5 kb and greater.
    Incubate the combination for a time sufficient to promote the precipitation and facilitated adsorption of the target DNA fragments selected for isolation to the paramagnetic microparticles.
    Remove the DNA fragment coated paramagnetic microparticles from the sample. For example, suitable magnetic means for the removal of the microparticles comprise exposing the microtiter sample plate to a magnetic field of about 1000 Gauss.
    Wash the microparticles three times with 250 ul of wash solution (70% EtOH, 10 mM EDTA).
    Air dry the washed microparticles
    Elute the purified DNA fragments selected for subcloning by contacting the washed microparticles with a suitable low ionic strength elution buffer, such as water.

Results

Electrophoresis: Electrophoretic analysis of the shattered fragment library resulting from hydroshearing indicates sheared DNA fragments ranging in size from 500 base pairs to 4.0 kb. Electrophoretic analysis of the nucleic acids eluted from the paramagnetic microparticles used to adsorb the target DNA fragments selected for isolation indicates fragments characterized by a molecular size of 1.5 kb and greater thus reducing the frequency of small inserts present in the library.

EXAMPLE 3

Use of PEG-Induced Size Selection to Prepare Post Nucleotide Sequencing Reaction Extension Products for Capillary Electrophoresis A conventional sequencing reaction comprises a mixture of a DNA template, numerous extension products, excess terminators or primers and nucleotides (e.g., both deoxy- and dideoxynucleotides) admixed with reagents (e.g., salts or alcohols). It is well known that the quality of the DNA sequence data, as assessed by average read length and unedited accuracy, is a direct correlate of the purity of the extension products used for electrophoretic analysis. Purity is an important factor for all sequencing methods, and is particularly crucial to the success of automated dye-labeled dideoxynucleotide sequencing methods. The following method has been used to prepare extension products (e.g., Sanger sequencing products) for capillary electrophoresis:

Transfer a 20 ul aliquot of detemplated fluorescently labeled dye terminator or dye primer sequencing products into a shallow well microtiter plate. The sequencing template can be removed using conventional methods (e.g., filtration) or by an alternative embodiment of the method described herein according to the method of Example 4.

Add 20 ul of prewashed carboxyl coated magnetic microparticles to the sequencing products.

Add 80 ul of Binding Buffer formulated to comprise PEG and salt concentrations which have been empirically determined to be sufficient to precipitate the target species of nucleic acid molecules present in the sequencing reaction. For the purposes of this example the Binding Buffer was 15% PEG 8000, 20 mM MgCl2.

Mix by shaking and incubate for a time sufficient to promote the precipitation and facilitated adsorption of the extension products to the microparticles.

Remove the paramagnetic microparticles by exposing the assay plate to a magnetic field of at least 1000 Gauss.

Wash the particle-bound extension products three times with 250 ul volumes of a wash solution comprising 70% EtOH 10 mM EDTA.

Air dry the washed microparticles.

Elute the purified sequencing products by contacting the washed with a small volume (e.g., 10 ul) of loading buffer (70% formamide, 10 mM EDTA or 12% pyrilidone).

Results

Sequencing: Sequencing product which had been purified using this procedure were then electrophoresed using an ABI 3700 capillary sequencer. For the dye terminator samples the electropherograms exhibited efficient removal of excess dye terminators and of short extension products below 25 bp. For dye primer samples the electropherograms exhibited efficient removal of excess dye primer and of short extension fragments below 25 base pairs. In both instances the electropherograms showed more normalized injection of different sized fragments than is exhibited using standard EtOH precipitation with the electrophoretic injection used in capillary electrophoresis.

Results

Electrophoresis: Extension products purified according to this procedure were then electrophoresed using an ABI 3700 capillary sequencer. For the dye terminator samples the electropherograms exhibited efficient removal of excess dye terminators and of short extension products below 25 base pears. For dye primer samples the electropherograms exhibited efficient removal of excess dye primer and of short extension fragments below 25 base pears. In both instances the electropherograms showed more normalized injection of different sized fragments than is exhibited using standard EtOH precipitation with the electrophoretic injection used in capillary electrophoresis.

EXAMPLE 4

Use of PEG-Induced Precipitation and Paramagnetic Microparticles to Remove a Template from a Nucleotide Sequencing Reaction Several capillary sequencers utilize electrophoretic injection to selectively inject the relatively smaller components of a sequencing reaction mixture. Therefore, it is imperative to detemplate the sequencing reaction mixture in order to attain effective injection of the extension products to be analyzed. Conventional methods of template removal employ membranes and consequently do not lend themselves to automation. Using the method described herein, an investigator of ordinary skill in the art can easily determine a protocol to selectively precipitate the DNA template, but not the relatively smaller sized extension fragments, under conditions which will facilitate the adsorption of the template to the surfaces of paramagnetic microparticles introduced into the mixture to facilitate the removal of the template from the reaction. For example the following procedure has been successfully used to detemplate Sanger sequencing reactions thereby producing a sample enriched for extension products:

Transfer 20 ul aliquots of either fluorescently labeled dye terminator or dye primer sequencing products into the wells of a shallow well microtiter plate.

Add 10 ul of prewashed carboxyl coated magnetic microparticles to the sequencing products.

Add 40 ul of Binding Buffer which has been empirically determined to be suitable for the selective precipitation of the DNA template targeted for isolation, but not extension products present in the same mixture. For example, a Binding Buffer comprising 11% PEG 8000, 1.1 M NaCl can be used.

Mix by shaking and incubated for a time sufficient to promote the precipitation and facilitated adsorption of the extension products to the microparticles.

Remove the paramagnetic microparticles by exposing the assay plate to a magnetic field of at least 1000 Gauss.

Wash the particle-bound extension products three times with 250 ul volumes of a wash solution comprising 70% EtOH 10 mM EDTA.

Air dry the washed microparticles.

Elute the purified sequencing products by contacting the washed with a small volume (e.g., 10 ul) of loading buffer (70% formamide, 1 mM EDTA).

Results

Electrophoresis: Sanger sequencing reaction products obtained using this procedure were placed on an agarose gel for electrophoretic analysis. Template and extension products are visible prior to cleanup, while only extension products are visible after. Readlengths assessed in phred 20s (99.0%) accuracy)=550 bp utilizing a ABI 377, 48 cm WTR, 10 hour gel. Phred 15 10 bp window from the end of trace falls at 716 bp.

EXAMPLE 5

Use of Alcohol Precipitation and Paramagnetic Microparticles for the Isolation of High Purity Extension Products Suitable for Capillary Electrophoresis The purity of extension products prepared for capillary sequencing can be even further improved by subjecting extension products selected according to the method of Example 3 to an alcohol-induced precipitation reaction performed under conditions suitable to promote the adsorption of the extension products targeted for isolation to paramagnetic microparticles. The ability to adsorb the extension products to a solid phase carrier facilitates an investigator's ability to wash the extension products free of any reagents and/or nucleotides present in the sequencing reaction. The presence of these components of the sequencing reaction are known to adversely effect the quality of the sequencing data obtained. For example the following protocol has been used to improve the purity of Sanger sequencing products, and concomitantly improve the quality of the resulting sequencing data:

Transfer 20 ul aliquots of either fluorescently labeled dye terminator or dye primer sequencing products into the wells of a shallow well microtiter plate.

Add 10 ul of prewashed carboxyl coated magnetic microparticles to the sequencing products.

Add 80 ul of Alcohol Precipitation Solution. For example, a 95% Ethanol or Isopropanol Solution can be used.

Mix by shaking and incubated for a time sufficient to promote the precipitation and facilitated adsorption of the extension products to the microparticles.

Remove the paramagnetic microparticles by exposing the assay plate to a magnetic field of at least 1000 Gauss.

Air dry the nucleic acid coated microparticles.

Elute the purified extension products with 10 ul 70% Formamide or 12% pyrrolidinone.

Results

Capillary

Electrophoresis: Sequencing products obtained using this procedure have a reduced representation of excess primer which aids in lane tracking and signal processing.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of selectively isolating a target species of nucleic acid molecules present in a mixture of nucleic acid molecules of different molecular sizes, wherein the target species is of a particular molecular size and wherein the target species is isolated in a salt concentration that is compatible with capillary electrophoresis, said method comprising the steps of:

(a) preparing a combination comprising the mixture of nucleic acid molecules, polyethylene glycol, salt, and solid phase carriers having a functional group-coated surface that reversibly binds nucleic acid molecules, wherein the polyethylene glycol and salt are present in sufficient concentrations to selectively precipitate the target species of nucleic acid molecule, but not other species of nucleic acid molecules having a molecular size which is less than the molecular size of the target species, thereby producing a first combination;

(b) maintaining the first combination under conditions appropriate for adsorption of the precipitated nucleic acid molecules to the functional group-coated surface of the solid phase carriers, thereby producing solid phase carriers having bound thereto the target species of nucleic acid molecules;

(c) removing the carriers having bound thereto the target species of nucleic acid molecules from the first combination, thereby producing a second mixture comprising the nucleic acid molecules having a molecular size which is less than the molecular size of the target species; and (d) eluting the target species of nucleic acid molecules from the carriers in a concentration of salt that is compatible with capillary electrophoresis.

2. The method of claim 1 wherein the mixture is selected from the group consisting of:

(a) a cell lysate prepared using cells obtained from mammalian tissue;

(b) a host cell lysate prepared from a cultured cell which has been transduced or transfected;

(c) a solution resulting from a PCR amplification procedure;

(d) a solution resulting from a post-DNA size shearing procedure;

(e) a solution resulting from a nucleotide sequencing reaction;

(f) a solution resulting from a restriction enzyme digestion comprising a mixture of nucleic acid molecule fragments; and (g) an agarose solution containing nucleic acid.

3. The method of claim 1 wherein the solid phase carriers having a functional group-coated surface that reversibly binds nucleic acid molecules are magnetically responsive solid phase carriers having a functional group-coated surface selected from the group consisting of: amine-coated, carboxyl-coated and encapsulated carboxyl group-coated paramagnetic microparticles.

4. The method of claim 1 wherein the solid phase carriers are removed from the combination or nucleic acid solution using a method selected from the group of methods consisting of: applying a magnetic field, applying vacuum filtration and centrifugation.

5. The method of claim 1 wherein the polyethylene glycol has an average molecular weight between about 6000 and about 10,000 and wherein the salt is selected from the group consisting of: sodium chloride, magnesium chloride, calcium chloride, potassium chloride, lithium chloride, barium chloride and cesium chloride.

6. The method according to claim 1 further comprising selectively isolating an additional target species of nucleic acid molecules from the second mixture, wherein the additional species is of smaller molecular size than the target species isolated in step (c), said method comprising the steps of:

(d) adding to the second mixture solid phase carriers having a functional group-coated surface that reversibly binds nucleic acid molecules, polyethylene glycol and salt, wherein the polyethylene glycol and salt are present in sufficient concentrations to precipitate the additional target species of nucleic acid molecule, thereby producing a second combination;

(e) maintaining the second combination under conditions appropriate for the adsorption of the additional target species of nucleic acid molecules to the functional group-coated surfaces of the solid phase carriers, thereby producing solid phase carriers having the additional target species of nucleic acid molecules bound thereto;

(f) removing the solid phase carriers having the additional species of nucleic acid molecules adsorbed thereto from the second combination; and (g) eluting the additional target species of nucleic acid molecules from the solid phase carriers, thereby selectively isolating an additional target species of nucleic acid molecules.

7. The method of claim 6 wherein the additional species of nucleic acid molecule targeted for isolation comprises at least about 25 base pairs.

8. A method of separating host cell DNA from exogenous DNA present in a host cell comprising the steps of:

(a) combining a host cell lysate with: (1) paramagnetic microparticles with a functional group-coated surface, (2) polyethylene glycol and (3) a salt, wherein polyethylene glycol and the salt are present in concentrations which result in binding of host cell DNA to the microparticles, but not in binding of exogenous DNA to the microparticles, thereby producing a first combination, which comprises host cell DNA bound to the microparticles and unbound exogenous DNA;

(b) separating the paramagnetic microparticles from the first combination, thereby producing a mixture that is enriched for exogenous DNA;

(c) adding to the mixture paramagnetic microparticles with a functional group-coated surface and polyethylene glycol at a concentration that results in binding of exogenous DNA to the microparticles, thereby producing a second combination, which comprises exogenous DNA bound to microparticles; and (d) separating the paramagnetic microparticles from the second combination, whereby exogenous DNA is separated from host cell DNA.

9. The method of claim 8 wherein the host cell is a mammalian cell and the exogenous nucleic acid is bacterial DNA, viral DNA, viral RNA or replicative form DNA.

10. The method of claim 9 wherein the exogenous nucleic acid comprises at least about 25 base pairs.

11. The method of claim 8 wherein the polyethylene glycol has an average molecular weight of about 8000, and the polyethylene glycol concentration of the first combination is between about 1% and about 4%, and the polyethylene glycol concentration of the second combination is at least 7%.

12. A method of separating plasmid DNA from high molecular weight DNA present in a host cell lysate comprising:

(a) preparing a suspension comprising carboxyl group-coated paramagnetic microparticles and a host cell lysate, wherein the host cell lysate comprises lysed host cells, low percentage PEG, and low molarity salt, wherein the PEG and salt are present in sufficient concentrations that high molecular weight DNA binds to the carboxyl group-coated paramagnetic microparticles, thereby producing a first combination comprising suspended paramagnetic microparticles having high molecular weight DNA bound thereto and unbound plasmid DNA;

(b) removing the paramagnetic microparticles from the first combination, thereby removing high molecular weight DNA from the first combination and producing a plasmid-enriched supernatant;

(c) adding to the plasmid-enriched supernatant carboxyl group-coated paramagnetic microparticles and sufficient polyethylene glycol to result in the binding of plasmid DNA to the paramagnetic microparticles, thereby producing a second combination; and (d) removing the paramagnetic microparticles having plasmid DNA bound thereto from the second combination, thereby separating plasmid DNA from high molecular weight DNA present in a host cell lysate.

13. The method of claim 12 wherein the plasmid DNA is recombinant DNA resulting from the replication of a vector selected from the group consisting of: a bacterial artificial chromosome, a yeast artificial chromosome, a phage artificial chromosome, a P1, a cosmid and a bacterial plasmid.

14. The method of claim 13, wherein the polyethylene glycol has an average molecular weight between about 6000 and about 10,000, and wherein the salt is selected from the group consisting of: sodium chloride, magnesium chloride, calcium chloride, potassium chloride, lithium chloride, barium chloride and cesium chloride.

15. An automatable method of producing plasmid DNA suitable for use as a template for nucleotide sequencing comprising the steps of:

(a) treating a host cell with an alkali and anionic detergent combination, thereby producing a lysed host cell suspension;

(b) combining the lysed host cell suspension with paramagnetic microparticles which bind DNA in the lysed host cell suspension with low percentage polyethylene glycol and low molarity salt, whereby host cell DNA is precipitated and binds to paramagnetic microparticles, thereby producing a first combination;

(c) removing paramagnetic microparticles having host cell DNA bound thereto from the first combination, thereby producing a plasmid-enriched supernatant;

(d) combining paramagnetic microparticles which bind DNA with the plasmid-enriched supernatant of (c), wherein the polyethylene glycol percentage and salt concentration are sufficient to result in binding of plasmid DNA to the paramagnetic microparticles, thereby producing a second combination;

(e) removing paramagnetic microparticles having plasmid DNA bound thereto from the second combination;

(f) washing the paramagnetic microparticles having plasmid DNA bound thereto with a wash buffer that dissolves impurities adsorbed to the paramagnetic microparticles but does not solubilize the plasmid DNA bound to the paramagnetic microparticles, thereby removing impurities adsorbed to the paramagnetic microparticles; and (g) contacting the paramagnetic microparticles of (f) with an elution buffer suitable for nucleotide sequencing, whereby plasmid DNA is released from the microparticles and dissolved in the elution buffer, thereby producing plasmid DNA suitable for use as a template for nucleotide sequencing.

16. The method of claim 15, wherein the host cell is selected from the group consisting of: a bacterial cell, a yeast cell, a plant cell and a mammalian cell.

17. The method of claim 16, wherein the plasmid DNA is recombinant DNA produced by the replication of a vector selected from the group consisting of: a bacterial artificial chromosome, a yeast artificial chromosome, a phage artificial chromosome, a P1, a cosmid and a bacterial plasmid.

18. The method of claim 17, wherein the plasmid DNA template comprises at least about 25 base pairs.

19. The method of claim 15 wherein the PEG has an average molecular weight between about 6000 and about 10,000, and wherein the salt is selected from the group consisting of: sodium chloride, magnesium chloride, calcium chloride, potassium chloride, lithium chloride, barium chloride and cesium chloride.

20. The method of claim 19 wherein the polyethylene glycol has an average molecular weight of about 8000 and the polyethylene glycol concentration of step (b) is between about 1% and about 4%, and the polyethylene glycol concentration of step (d) is at least 7%.

21. A kit for high through-put automated DNA template production comprising:

(a) reagents for preparing a host cell lysate;

(b) an aqueous solution of functional group-coated paramagnetic microparticles; and (c) at least one binding buffer formulated to comprise a suitable salt and a suitable polyethylene glycol, wherein the salt and the polyethylene glycol are each present at a concentration appropriate for binding a nucleic acid species characterized by a particular molecular size to the microparticles or reagents for the formulation of a suitable buffer.

22. The kit of claim 21 wherein the kit additionally comprises reagents for the formulation of a wash buffer and an elution buffer, wherein the wash buffer dissolves impurities, but not nucleic acids bound to paramagnetic microparticles and the elution buffer is a low ionic strength buffer.

23. The kit of claim 22 wherein the kit further comprises a magnetic plate holder appropriate for applying a magnetic field of at least about 1000 Gauss to the wells of a microtiter plate, wherein said magnet comprises at least one N35 magnet.

24. A method of selectively isolating extension products from a sequencing reaction mixture, comprising the steps of:

(a) preparing a combination comprising (1) an aliquot of labeled energy transfer dye terminator or dye primer nucleotide sequencing reaction products comprising extension products; (2) carboxyl-coated paramagnetic microparticles and (3) a nucleic acid precipitating agent, wherein the precipitating reagent is present in sufficient concentration to selectively precipitate the extension products, but not other nucleic acid having a molecular size which is smaller than the molecular size of the extension products in the reaction mixture;

(b) maintaining the combination under conditions appropriate for adsorption of the precipitated extension products to the functional group-coated surface of the microparticles, thereby producing extension product-coated microparticles;

(c) removing the extension product-coated microparticles from the combination;

(d) eluting the extension products from the microparticles; and (e) removing the solid phase carriers from the solution of (e), whereby the extension products of a sequencing reaction mixture are selectively isolated.

25. The method according to claim 24, wherein the extension products comprises at least about 25 base pairs.

26. The method of claim 24, wherein the nucleic acid precipitating reagent is polyethylene glycol having an average molecular weight between about 6000 and about 10,000, and wherein the salt is selected from the group consisting of: sodium chloride, magnesium chloride, calcium chloride, potassium chloride, lithium chloride, barium chloride and cesium chloride.

27. The method of claim 24, wherein the nucleic acid precipitating reagent is ethanol or isopropanol.

28. A method of selectively isolating a target species of nucleic acid molecules present in a mixture of nucleic acid molecules of different molecular sizes, wherein the target species is of a particular molecular size, said method comprising the steps of:

(a) preparing a combination comprising the mixture of nucleic acid molecules, polyethylene glycol, salt, and solid phase carriers having a functional group-coated surface that reversibly binds nucleic acid molecules, wherein the polyethylene glycol and salt are present in sufficient concentrations to selectively precipitate the target species of nucleic acid molecule, but not other species of nucleic acid molecules having a molecular size which is less than the molecular size of the target species, thereby producing a first combination;

(b) maintaining the first combination under conditions appropriate for adsorption of the precipitated nucleic acid molecules to the functional group-coated surface of the solid phase carriers, thereby producing solid phase carriers having bound thereto the target species of nucleic acid molecules;

(c) removing the carriers having bound thereto the target species of nucleic acid molecules from the first combination, thereby producing a second mixture comprising the nucleic acid molecules having a molecular size which is less than the molecular size of the target species; and (d) eluting the target species of nucleic acid molecules from the carriers.

29. The method of claim 28 wherein the mixture is selected from the group consisting of:

(a) a cell lysate prepared using cells obtained from mammalian tissue;

(b) a host cell lysate prepared from a cultured cell which has been transduced or transfected;

(c) a solution resulting from a PCR amplification procedure;

(d) a solution resulting from a post-DNA size shearing procedure;

(e) a solution resulting from a nucleotide sequencing reaction;

(f) a solution resulting from a restriction enzyme digestion comprising a mixture of nucleic acid molecule fragments; and (g) an agarose solution containing nucleic acid.

30. The method of claim 28 wherein the solid phase carriers having a functional group-coated surface that reversibly binds nucleic acid molecules are magnetically responsive solid phase carriers having a functional group-coated surface selected from the group consisting of: amine-coated, carboxyl-coated and encapsulated carboxyl group-coated paramagnetic microparticles.

31. The method of claim 28 wherein the solid phase carriers are removed from the combination or nucleic acid solution using a method selected from the group of methods consisting of: applying a magnetic field, applying vacuum filtration and centrifugation.

32. The method of claim 28 wherein the polyethylene glycol PEG has an average molecular weight between about 6000 and about 10,000, and wherein the salt is selected from the group consisting of: sodium chloride, magnesium chloride, calcium chloride, potassium chloride, lithium chloride, barium chloride and cesium chloride.

33. The method according to claim 28 further comprising selectively isolating an additional target species of nucleic acid molecules from the second mixture, wherein the additional species is of smaller molecular size than the target species isolated in step (c), said method comprising the steps of:

(d) adding to the second mixture solid phase carriers having a functional group-coated surface that reversibly binds nucleic acid molecules, polyethylene glycol and salt, wherein the polyethylene glycol and salt are present in sufficient concentrations to precipitate the additional target species of nucleic acid molecule, thereby producing a second combination;

(e) maintaining the second combination under conditions appropriate for the adsorption of the additional target species of nucleic acid molecules to the functional group-coated surfaces of the solid phase carriers, thereby producing solid phase carriers having the additional target species of nucleic acid molecules bound thereto;

(f) removing the solid phase carriers having the additional species of nucleic acid molecules adsorbed thereto from the second combination; and (g) eluting the additional target species of nucleic acid molecules from the solid phase carriers, thereby selectively isolating an additional target species of nucleic acid molecules.

34. The method of claim 33 wherein the additional species of nucleic acid molecule targeted for isolation comprises at least about 25 base pairs.

* * * * *